(12) United States Patent
Anderson et al.

(10) Patent No.: US 10,593,001 B2
(45) Date of Patent: Mar. 17, 2020

(54) APPARATUS, SYSTEM AND METHOD FOR GENERATING AND DISPLAYING A TREATMENT PROTOCOL

(71) Applicant: OPTUMINSIGHT, INC., Eden Prairie, MN (US)

(72) Inventors: David R. Anderson, Chaska, MN (US); Jean Rawlings, Roy, UT (US)

(73) Assignee: OPTUMINSIGHT, INC., Eden Prairie, MN (US)

( * ) Notice: Subject to any disclaimer, the term of this patent is extended or adjusted under 35 U.S.C. 154(b) by 449 days.

(21) Appl. No.: 15/624,250

(22) Filed: Jun. 15, 2017

(65) Prior Publication Data

US 2017/0286609 A1    Oct. 5, 2017

Related U.S. Application Data

(63) Continuation of application No. 12/562,608, filed on Sep. 18, 2009, now abandoned.

(60) Provisional application No. 61/098,185, filed on Sep. 18, 2008.

(51) Int. Cl.

| G06Q 50/22 | (2018.01) |
| G16H 50/70 | (2018.01) |
| G16H 50/50 | (2018.01) |
| G06Q 10/10 | (2012.01) |
| G16H 15/00 | (2018.01) |
| G16H 50/20 | (2018.01) |
| G06F 19/00 | (2018.01) |

(52) U.S. Cl.
CPC ............. *G06Q 50/22* (2013.01); *G06Q 10/10* (2013.01); *G16H 50/50* (2018.01); *G16H 50/70* (2018.01); *G06F 19/328* (2013.01); *G16H 15/00* (2018.01); *G16H 50/20* (2018.01)

(58) Field of Classification Search
CPC ........ G16H 50/20; G16H 10/60; G16H 15/00; G16H 40/20; G16H 50/50; G16H 50/70; G06Q 50/22; G06Q 50/24; G06Q 10/0635; G06Q 10/0637; G06Q 10/10; G06Q 10/1095; G06F 19/328; G06F 19/3418; G06F 19/3456; G06F 19/3481; G06F 19/00; G06F 19/324; G06F 19/325; G06F 19/322; G06F 19/327; G06F 19/345
See application file for complete search history.

(56) References Cited

U.S. PATENT DOCUMENTS

| 5,835,897 A * | 11/1998 | Dang ................... G06F 19/328 705/2 |
| 6,108,635 A * | 8/2000 | Herren .................. G06Q 40/08 705/2 |
| 6,234,964 B1 * | 5/2001 | Iliff ..................... G06F 19/3418 600/300 |

(Continued)

*Primary Examiner* — Neal Sereboff
(74) *Attorney, Agent, or Firm* — Seyfarth Shaw LLP; Brian Michaelis

(57) ABSTRACT

A relationship management device and method providing a user interface containing treatment protocol for an individual comprising: (a) a user interface electrically connected with a data storage device; (b) a server electrically connected with the user interface and the data storage device; and (c) a treatment processor electrically connected with the server, wherein the treatment processor is configured to generate an optimized treatment protocol for the individual.

9 Claims, 17 Drawing Sheets

(56) References Cited

U.S. PATENT DOCUMENTS

| | | | |
|---|---|---|---|
| 6,370,511 B1 * | 4/2002 | Dang | G06F 19/328 |
| | | | 705/2 |
| 7,379,885 B1 * | 5/2008 | Zakim | G06F 19/325 |
| | | | 705/2 |
| 2003/0127390 A1 * | 7/2003 | Davis, Jr. | A61M 1/3413 |
| | | | 210/646 |
| 2004/0143461 A1 * | 7/2004 | Watkins | G06Q 50/22 |
| | | | 705/2 |
| 2005/0289092 A1 * | 12/2005 | Sumner, II | G06F 19/3481 |
| | | | 706/46 |
| 2007/0122824 A1 * | 5/2007 | Tucker | G06Q 50/22 |
| | | | 435/6.17 |
| 2008/0183500 A1 * | 7/2008 | Banigan | G06Q 50/24 |
| | | | 705/3 |
| 2009/0125331 A1 * | 5/2009 | Pamsgaard | A61K 31/343 |
| | | | 705/3 |

* cited by examiner

1100

Jenny, other people like you who are sick have seen the following physicians:

All About You

Medical

- Caring about myself
- What decisions do I need to make today

Non-Medical

- Lifetime claims costs
- Yearly claims costs
- Will Yoga help
- Wellness programs I should consider
- Financial Planning

Tools and Information

- Saving Calculator
- A guide to use when talking to your doctor
- Condition Cost Estimator
- What type of benefit plan is right for me?

Doctor's Name

Anita D. Stephenson, MD
Specialty: Orthopedic Surgery
Gender: Female
Years in Practice: 25
Hospital Affiliation: Fairview Southdale Hospital, Methodist Hospital, Abbott Northwestern Hospital
Accepts Premier PPO Plus: Yes
Accepting New Patients: Yes Patrick A. Drake, MD
Specialty: Orthopedic Surgery
Gender: Male
Years in Practice: 35
Hospital Affiliation: Abbott Distance From You 4 Miles
825 Main Street
Suite 300
Eden Prairie, MN 55344
(952) 463-8744
Directions
3 Additional Addresses 17 Miles
727 Metcalf Road
Minneapolis, MN 55360
(952) 833-8700
Directions

Hello Jenny,

Are you wondering?
Is this caused by Zocor?
Is this normal a year after intestinal surgery?
Whether or not it is too early for flu season in your area?
Nurseline: 800-123-4567
Plan Name: PPO+

Staying Healthy:

- My Health Map: See "you are here" marker

Common Questions more

- How much is an office visit?
- What can I expect?
- Can I use my flex spending card?

Related Articles more

- Flu season comes early to MN

FIG. 11

APPARATUS, SYSTEM AND METHOD FOR GENERATING AND DISPLAYING A TREATMENT PROTOCOL

CROSS-REFERENCE TO RELATED APPLICATIONS

This application is a continuation of U.S. application Ser. No. 12/562,608, filed on Sep. 18, 2009, which claims the benefit of U.S. Provisional Application No. 61/098,185 filed Sep. 18, 2008, the entire contents of application Ser. No. 12/562,608 and Application No. 61/098,185 are specifically incorporated herein by reference without disclaimer.

BACKGROUND OF THE INVENTION

Field of the Invention

This invention relates to disease identification and management and more particularly relates to an apparatus system and method for presenting a natural history and natural progression of disease.

Description of the Related Art

Most typical health treatment plans are reactive rather than proactive. For example, a physician typically only treats patients for symptoms or diseases that have presented. Even when there are known relationships between diseases or symptoms, these diseases and symptoms are often left untreated until they present in a patient.

Some resources available to physicians present treatment plans or protocols for physicians treating patients with certain diseases. Although such treatment plans are often helpful, they typically do not present a clear picture of the disease from start to finish, and they often fail to provide the physician with assistance in determining the patient's current status within a typical progression of the disease.

It is important for a treating physician to have a clear understanding, not only of the disease progression and possible treatments, but also of the patient's status within the progression, so that the proper treatments and tests are administered at appropriate times. Additionally, it is useful for the patient to have a clear understanding of the disease progression, and their current status, so that they can plan for future expenses, complications, and treatments.

Similarly, health insurance companies may wish to identify a patient's status within their disease progression, so that they are more able to assist their customers by suggesting preventative treatments or procedures, allocate expenses, and the like.

In a further embodiment, it may be useful for healthcare researchers to identify a patient's status within a disease progression, along with typical decision points and historical outcomes, so that better treatment plans, protocols, medications, and procedures may be developed.

Additionally, physicians may be able to use such treatment plans and protocols to take a proactive, rather than reactive, approach to healthcare and disease management.

The referenced shortcomings are not intended to be exhaustive, but rather are among many that tend to impair the effectiveness of previously known techniques disease management; however, those mentioned here are sufficient to demonstrate that the methodologies appearing in the art have not been satisfactory and that a significant need exists for the techniques described and claimed in this disclosure.

SUMMARY OF THE INVENTION

From the foregoing discussion, it should be apparent that a need exists for an apparatus, system, and method for presentation of a natural history and the progression pathway of a disease.

An apparatus for presentation of a natural history and the progression pathway of a disease is presented. In one embodiment, the apparatus includes an input/output adapter configured to receive information to generate a health profile for an individual. The apparatus may also include a processor configured to retrieve a disease progression map comprising one or more disease progression states from a data storage device, and determine a disease progression state associated with the individual in response to the health profile. In a further embodiment, the apparatus may include a display adapter coupled to the state determination module, the display module configured to display a graphical representation of the disease progression state with reference to the disease progression map.

A computer program product comprising a computer readable medium having computer usable program code comprising computer operable software modules is also presented. In one embodiment, the modules may include a profile module, a disease progression module, a state determination module, and a display module. The profile module may generate a health profile for an individual. In one embodiment, the disease progression module may retrieve a disease progression map comprising one or more disease progression states from a data storage device. The state determination module may determine a disease progression state associated with the individual in response to the health profile. Additionally, the display module may display a graphical representation of the disease progression state with reference to the disease progression map.

In a further embodiment, the profile module may include an automatic profile generator configured to automatically generate the health profile for the individual from data previously stored in association with the individual. In a further embodiment, the profile module may include an interactive profile generator configured to generate the health profile in response to data entered by a user regarding the individual through an interactive display.

In one embodiment, the state determination module may include a question predictor module configured to predict one or more questions that the individual may have regarding their health state in response to the determination of the disease progression state associated with the individual. The state determination module may also include a cost analysis module configured to analyze costs associated with one or more disease progression scenarios based on the disease progression state associated with the individual. In a further embodiment, the state determination module may include a treatment protocol generator configured to determine an optimized treatment protocol for the individual in response to the disease progression state associated with the individual. Additionally, the state determination module may include a co-morbidity analyzer configured to identify a potential co-morbidity with an increased probability of presentation as a result of the disease progression state associated with the individual.

In one embodiment, the display module may include a chart presenter configured to display one or more graphical charts representing information generated by the state determination module.

A system is also presented for presentation of a natural history and the progression pathway of a disease. In one embodiment, the system may include a data storage device configured to store one or more disease progression maps, the disease progression maps comprising one or more disease progression states. The system may also include a server. In one embodiment, the server may include a profile module configured to generate a health profile for an individual, a disease progression module configured to retrieve a disease progression map comprising one or more disease progression states from the data storage device, a state determination module configured to determine a disease progression state associated with the individual in response to the health profile, and a display module configured to display a graphical representation of the disease progression state with reference to the disease progression map.

A method is also presented for presentation of a natural history and the progression pathway of a disease. The method in the disclosed embodiments substantially includes the steps necessary to carry out the functions presented above with respect to the operation of the described apparatus and system. In one embodiment, the method includes generating a health profile for an individual, retrieving a disease progression map comprising one or more disease progression states from a data storage device, determining a disease progression state associated with the individual in response to the health profile, and displaying a graphical representation of the disease progression state with reference to the disease progression map.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 11 is a screen-shot diagram illustrating another embodiment of a user interface display;

DETAILED DESCRIPTION

Figure 1:
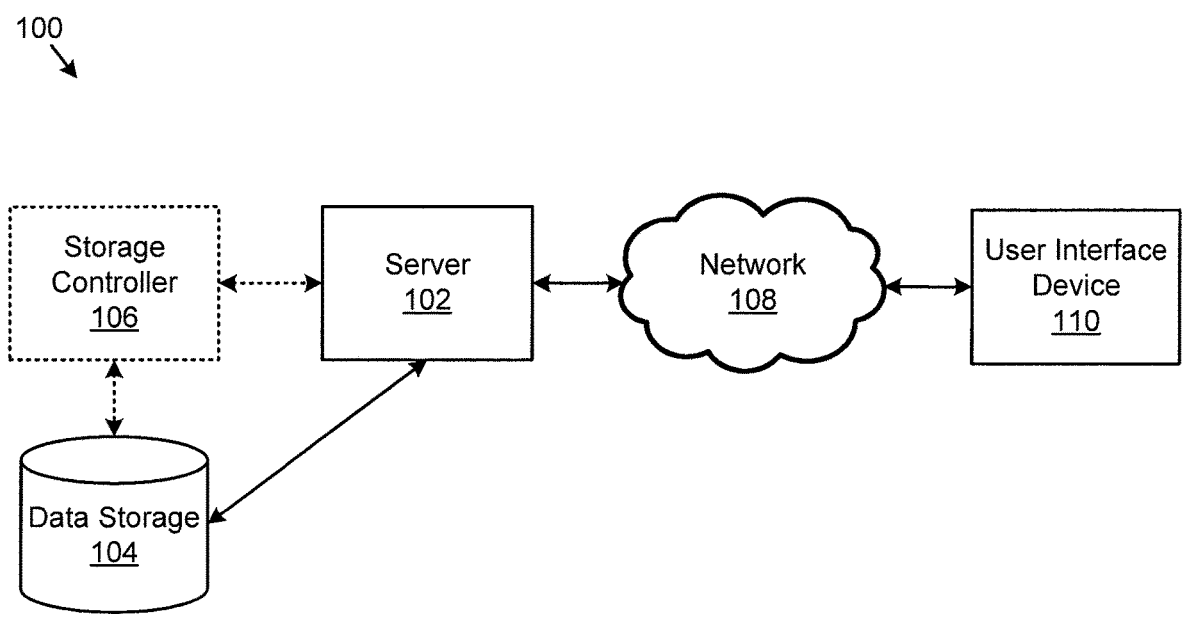
FIG. 1 is a schematic block diagram illustrating one embodiment of a system for presenting a natural history and progression pathway of a disease.

The invention and the various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

FIG. 1 illustrates one embodiment of a system 100 for presenting a natural history of a disease. The system 100 may include a server 102 a data storage device 104, a network 108, and a user interface device 110. In a further embodiment, the system 100 may include a storage controller 106 or storage server configured to manage data communications between the data storage device 104 and the server 102 or other components in communication with the network 108. In an alternative embodiment, the storage controller 106 may be coupled to the network 108. In a general embodiment, the system 100 may facilitate identification of patterns in a progression of a disease. Specifically, the system 100 may obtain user inputs, retrieve stored information related to the individual, search for and identify a physician or service provider that is a best match for the individual, identify historical "twins" or individuals with similar histories, identify cohorts, determine the individuals attitudes toward certain services or programs, determine possible answers to questions that the user may be considering, determine health trajectories or likely progressions of the individual's disease, determine life expectancy, determine cost information , and the like.

In one embodiment, the user interface device 110 is referred to broadly and is intended to encompass a suitable processor-based device such as a desktop computer, a laptop computer, a Personal Digital Assistant (PDA), a mobile communication device or organizer device having access to the network 108. In a further embodiment, the user interface device 110 may access the Internet to access a web application or web service hosted by the server 102 and provide a user interface for enabling the service consumer (user) to enter personal information. For example, the user may enter identifying credentials or login information, disease symptoms, questions, search terms, or the like.

The network 108 may facilitate communications of data between the server 102 and the user interface device 110. The network 108 may include any type of communications network including, but not limited to a direct PC to PC connection, a local area network (LAN), a wide area network (WAN), a modem to modem connection, the Internet, a combination of the above, or any other communications network now known or later developed within the networking arts which permits two or more computers to communicate, one with another.

In one embodiment, the server 102 is configured to generate a health profile for an individual, retrieve a disease progression map comprising one or more disease progression states from a data storage device, determine a disease progression state associated with the individual in response to the health profile, and display a graphical representation of the disease progression state with reference to the disease progression map. Additionally, the server may access data stored in the data storage device 104 via a Storage Area Network (SAN) connection, a LAN, a data bus, or the like.

The data storage device 104 may include a hard disk, including hard disks arranged in an Redundant Array of Independent Disks (RAID) array, a tape storage drive comprising a plurality of magnetic tape data storage devices, an optical storage device, or the like. In one embodiment, the data storage device 104 may store health related data, such as insurance claims data, consumer data, or the like. The data may be arranged in a database and accessible through Structured Query Language (SQL) queries, or other data base query languages or operations.

Figure 2:
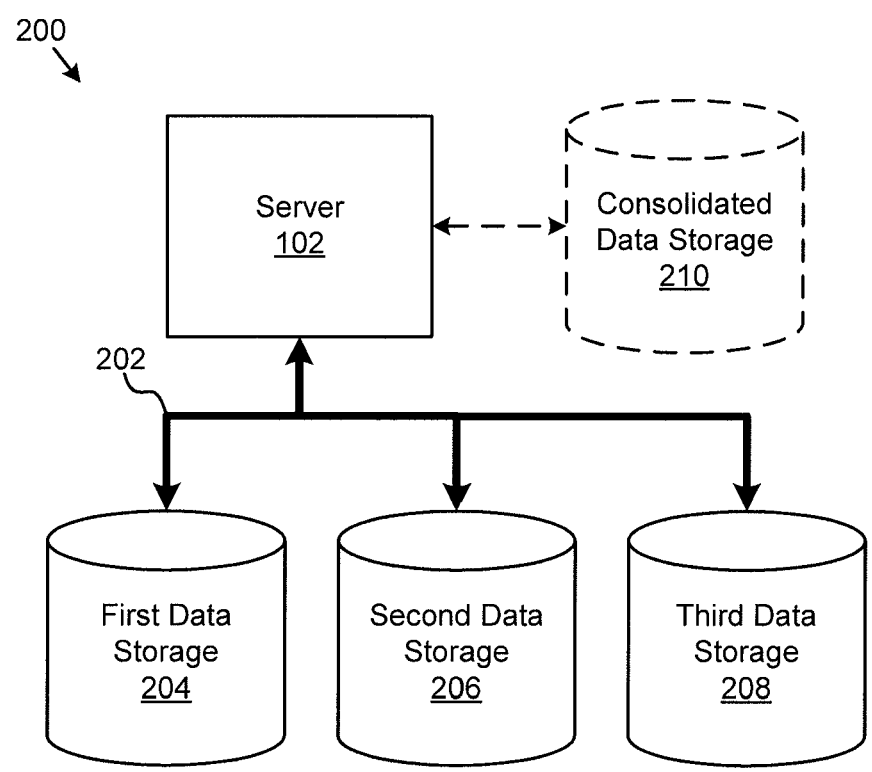
FIG. 2 is a schematic block diagram illustrating one embodiment of a database system for storing data used in presenting a natural history and progression pathway of a disease.

FIG. 2 illustrates one embodiment of a data management system 200 configured to store and manage data for generating a natural history of a disease. In one embodiment, the system 200 may include a server 102. The server 102 may be coupled to a data-bus 202. In one embodiment, the system 200 may also include a first data storage device 204, a second data storage device 206 and/or a third data storage device 208. In further embodiments, the system 200 may include additional data storage devices (not shown). In such an embodiment, each data storage device 204-208 may host a separate database of customer information. The customer information in each database may be keyed to a common field or identifier, such as an individual's name, social security number, customer number, or the like. Alternatively, the storage devices 204-208 may be arranged in a RAID configuration for storing redundant copies of the database or databases.

In one embodiment, the server 102 may submit a query to each of the data storage devices 204-206 to collect a consolidated set of data elements associated with an individual or group of individuals. The server 102 may store the consolidated data set in a consolidated data storage device 210. In such an embodiment, the server 102 may refer back to the consolidated data storage device 210 to obtain a set of data elements associated with a specified individual. Alternatively, the server 102 may query each of the data storage devices 204-208 independently or in a distributed query to obtain the set of data elements associated with a specified individual. In another alternative embodiment, multiple databases may be stored on a single consolidated data storage device 210.

In various embodiments, the server 102 may communicate with the data storage devices 204-210 over the data-bus 202. The data-bus may comprise a SAN, a LAN, or the like. The communication infrastructure may include Ethernet, Fibre-Chanel Arbitrated Loop (FC-AL), Small Computer System Interface (SCSI), and/or other similar data communication schemes associated with data communication. For example, there server 102 may communicate indirectly with the data storage devices 204-210; the server first communicating with a storage server or storage controller 106.

In one example of the system 200, the first data storage device 204 may store data associated with insurance claims made by one or more individuals. The insurance claims data may include data associated with medical services, procedures, and prescriptions utilized by the individual. In one particular embodiment, the first data storage device 202 included insurance claims data for over 56 million customers of a health insurance company. The database included claims data spanning over 14 years. Of those 56 million members, 26 million had a five year history or more. In one embodiment, individuals suffering from a common illness may be aggregated to identify many, if not all, of the possible decisions points and their resulting outcomes related to the progression of the disease.

In one embodiment, the second data storage device 206 may store summary data associated with the individual. The summary data may include one or more diagnoses of conditions from which the individual suffers and/or actuarial data associated with an estimated cost in medical services that the individual is likely to incur. The third data storage device 208 may store customer service and program service usage data associated with the individual. For example, the third data storage device 208 may include data associated with the individual's interaction or transactions on a website, calls to a customer service line, or utilization of a preventative medicine health program. A fourth data storage device (not shown) may store marketing data. For example, the marketing data may include information relating to the individual's income, race or ethnicity, credit ratings, etc. In one embodiment, the marketing database may include marketing information available from a commercial direct marketing data provider.

The server 102 may host a software application configured for generating a natural history of a disease. The software application may further include modules or functions for interfacing with the data storage devices 204-210, interfacing a network 108, interfacing with a user, and the like. In a further embodiment, the server 102 may host an engine, application plug-in, or application programming interface (API). In another embodiment, the server 102 may host a web service or web accessible software application.

Figure 3:
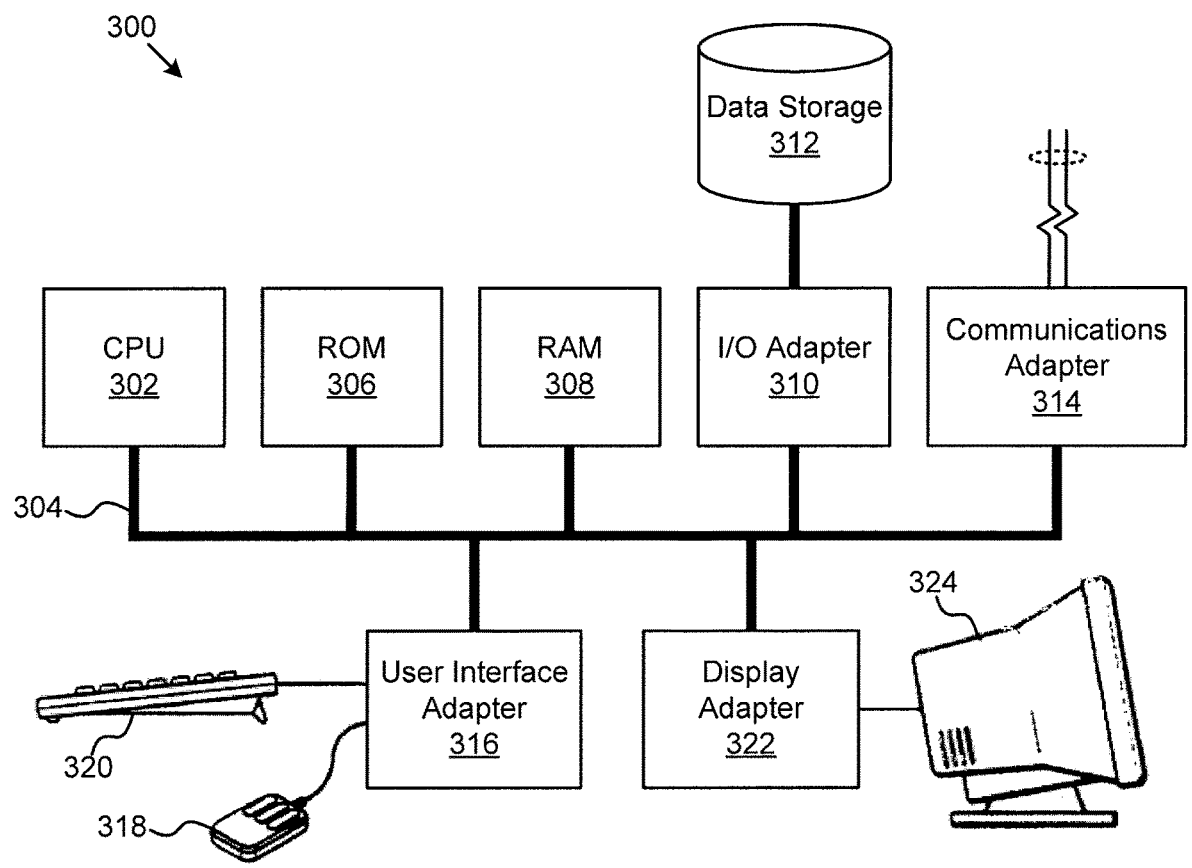
FIG. 3 is a schematic block diagram illustrating one embodiment of a computer system that may be used in accordance with certain embodiments of the system for presenting a natural history and progression pathway of a disease.

FIG. 3 illustrates a computer system 300 adapted according to certain embodiments of the server 102 and user interface device 110. The central processing unit (CPU) 302 is coupled to the system bus 304. The CPU 302 may be a general purpose CPU or microprocessor. The present embodiments are not restricted by the architecture of the CPU 302 as long as the CPU 302 supports the modules and operations as described herein. The CPU 302 may execute the various logical instructions according to the present embodiments. For example, the CPU 302 may execute machine-level instructions according to the exemplary operations described below with reference to FIG. 8.

The computer system 300 also may include Random Access Memory (RAM) 308, which may be SRAM, DRAM, SDRAM, or the like. The computer system 300 may utilize RAM 308 to store the various data structures used by a software application configured to present a natural history of a disease. The computer system 300 may also include Read Only Memory (ROM) 306 which may be PROM, EPROM, EEPROM, or the like. The ROM may store configuration information for booting the computer system 300. The RAM 308 and the ROM 306 hold user and system 100 data.

The computer system 300 may also include an input/output (I/O) adapter 310, a communications adapter 314, a user interface adapter 316, and a display adapter 322. The I/O adapter 310 and/or user the interface adapter 316 may, in certain embodiments, enable a user to interact with the computer system 300 in order to input information for authenticating a user, identifying an individual, or receiving health profile information. In a further embodiment, the display adapter 322 may display a graphical user interface associated with a software or web-based application for presenting a natural history of a disease.

The I/O adapter 310 may connect to one or more storage devices 312, such as one or more of a hard drive, a Compact Disk (CD) drive, a floppy disk drive, a tape drive, to the computer system 300. The communications adapter 314 may be adapted to couple the computer system 300 to the network 106, which may be one or more of a LAN and/or WAN, and/or the Internet. The user interface adapter 316 couples user input devices, such as a keyboard 320 and a pointing device 318, to the computer system 300. The display adapter 322 may be driven by the CPU 302 to control the display on the display device 324.

The present embodiments are not limited to the architecture of system 300. Rather the computer system 300 is provided as an example of one type of computing device that may be adapted to perform the functions of server 102 and user interface device 110. For example, any suitable processor-based device may be utilized including without limitation, including personal data assistants (PDAs), computer game consoles, and multi-processor servers. Moreover, the present embodiments may be implemented on application specific integrated circuits (ASIC) or very large scale integrated (VLSI) circuits. In fact, persons of ordinary skill in the art may utilize any number of suitable structures capable of executing logical operations according to the described embodiments.

Figure 4:
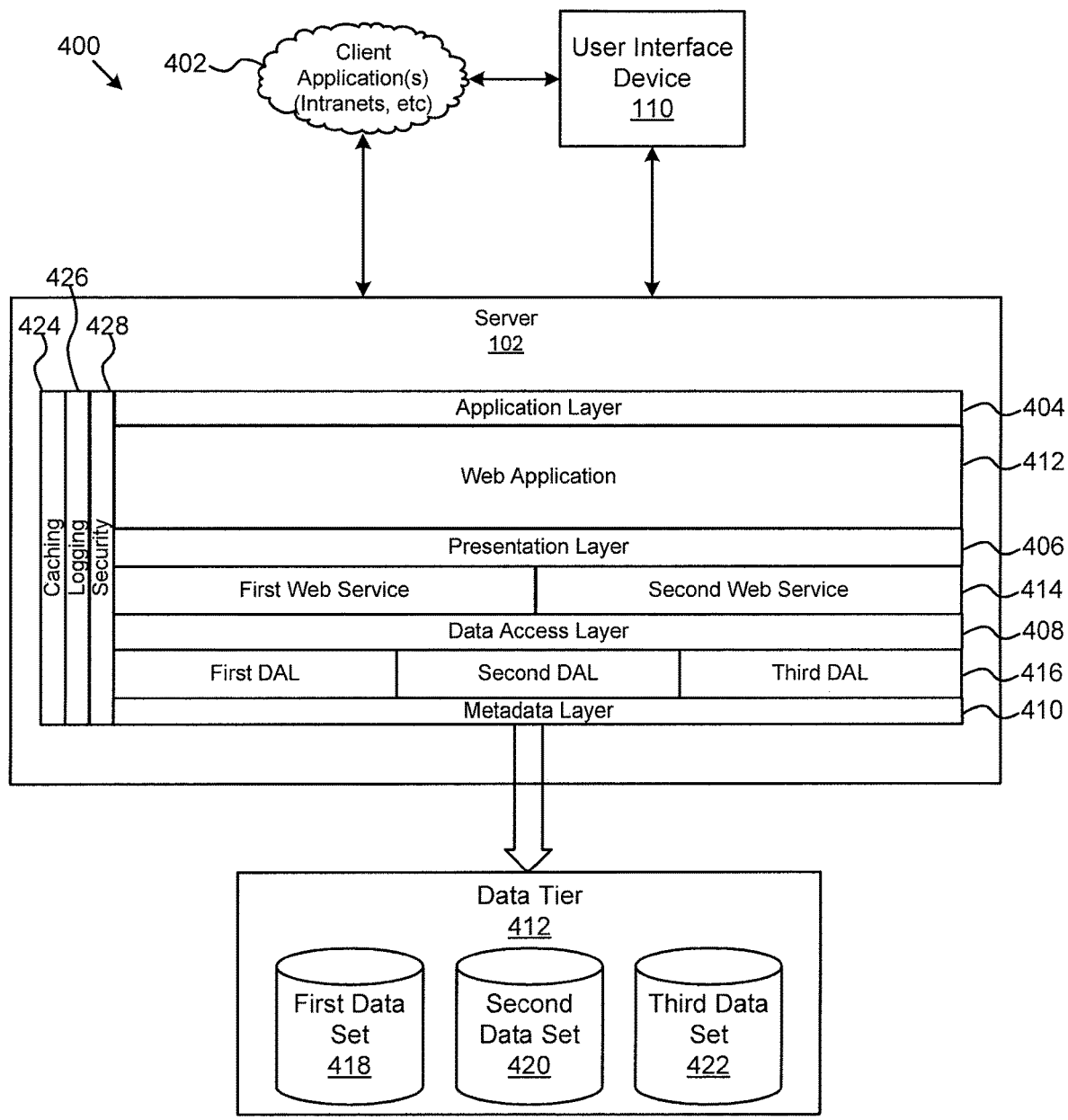
FIG. 4 is a schematic logical diagram illustrating the various layers of operation in a system for presenting a natural history and progression pathway of a disease.

FIG. 4 illustrates one embodiment of a network-based system 400 for presenting a natural history or progression of a disease. In one embodiment, the network-based system 400 includes a server 102. Additionally, the network-based system 400 may include a user interface device 110. In still a further embodiment, the network-based system 400 may include one or more network-based client applications 402 configured to be operated over a network 108 including an intranet, the Internet, or the like. In still another embodiment, the network-based system 400 may include one or more data storage devices 104.

The network-based system 400 may include components or devices configured to operate in various network layers. For example, the server 102 may include modules configured to work within an application layer 404, a presentation layer 406, a data access layer 408 and a metadata layer 410. In a further embodiment, the server 102 may access one or more data sets 422-422 that comprises a data layer or data tier 412. For example, a first data set 422, a second data set 420 and a third data set 422 may comprise data tier 412 that is stored on one or more data storage devices 204208.

One or more web applications 412 may operate in the application layer 404. For example, a user may interact with the web application 412 though one or more I/O interfaces 318, 320 configured to interface with the web application 412 through an I/O adapter 310 that operates on the application layer. In one particular embodiment, a web application 412 may be provided for presenting a natural progression of a disease that includes software modules configured to perform the steps of generate a health profile for an individual, retrieve a disease progression map comprising one or more disease progression states from a data storage device, determine a disease progression state associated with the individual in response to the health profile, and display a graphical representation of the disease progression state with reference to the disease progression map.

In a further embodiment, the server 102 may include components, devices, hardware modules, or software modules configured to operate in the presentation layer 406 to support one or more web services 414. For example, a web application 412 may access a web service 414 to perform one or more web-based functions for the web application 412. In one embodiment, a web application 412 may operate on a first server 102 and access one or more web services 414 hosted on a second server (not shown) during operation.

For example, a web application 412 for presenting charts, graphs, treatment plans, or other information may access a first web service 414 for locating a twin associated with an individual and a second web service 414 for locating a cohort associated with the individual. The web services 414 may receive an identifier associated with the individual as an input and return an identifier associated with the twin or the cohort as an output. Alternatively, the web service 414 may return data associated with the twin or cohort for analysis. One of ordinary skill in the art will recognize various web-based architectures employing web services 414 for modular operation of a web application 412.

In one embodiment, a web application 412 or a web service 414 may access one or more of the data sets 418-422 through the data access layer 408. In certain embodiments, the data access layer 408 may be divided into one or more independent data access layers 416 for accessing individual data sets 418-422 in the data tier 412. These individual data access layers 416 may be referred to as data sockets or adapters. The data access layers 416 may utilize metadata from the metadata layer 410 to provide the web application 412 or the web service 414 with specific access to the data set 412.

For example, the data access layer 416 may include operations for performing a query of the data sets 418-422 to retrieve specific information for the web application 412 or the web service 414. In a more specific example, the data access layer 416 may include a query for identifying claim information associated with an individual, a twin associated with the individual, or a cohort associated with the individual.

Figure 5:
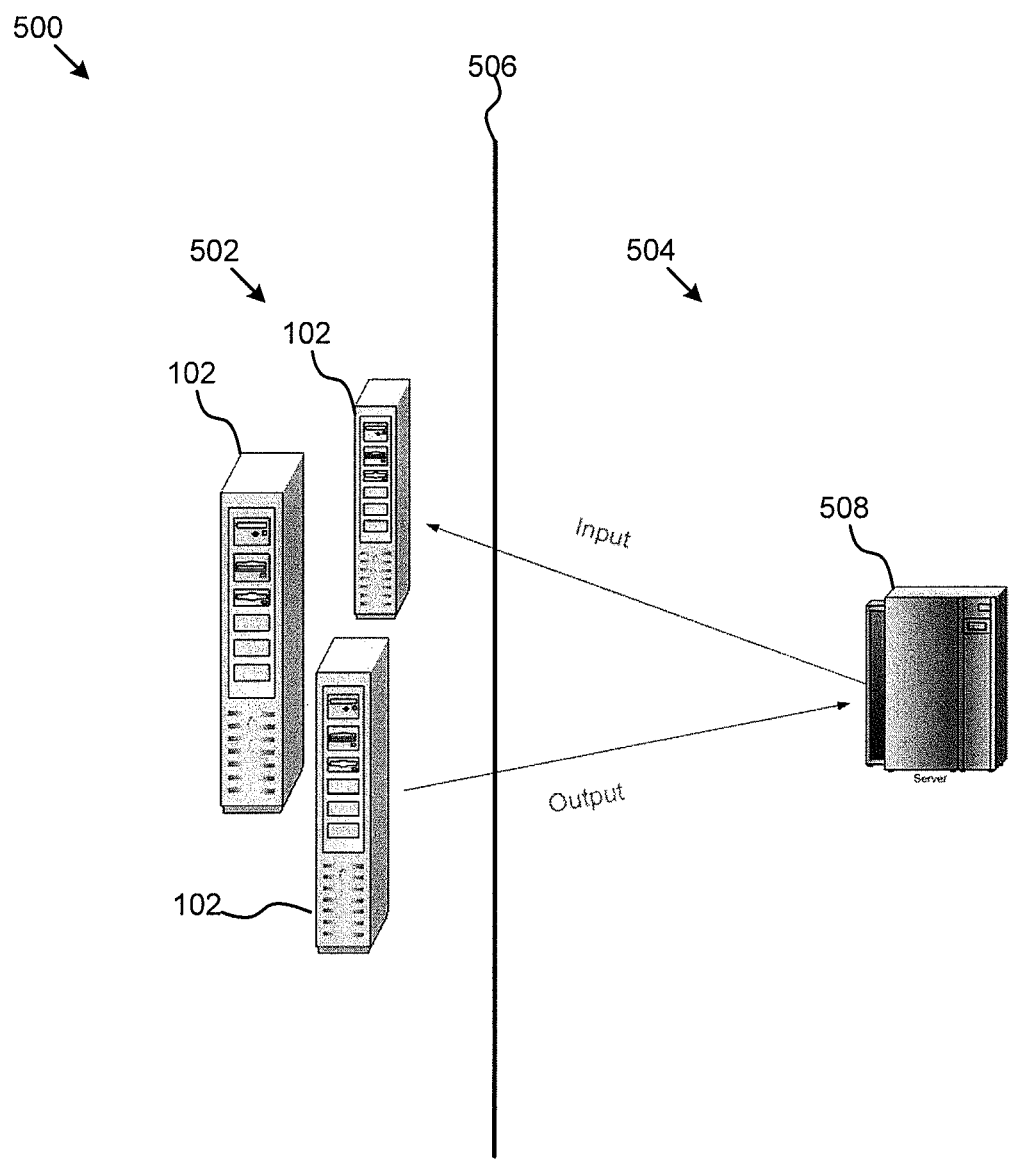
FIG. 5 is a schematic block diagram illustrating another embodiment of a system for presenting a natural history of a disease.

FIG. 5 illustrates a further embodiment of a system 500 for presenting a natural history of a disease. In one embodiment, the system 500 may include a service provider site 502 and a client site 504. The service provider site 502 and the client site 504 may be separated by a geographic separation 506.

In one embodiment, the system 500 may include one or more servers 102 configured to host a software application 412 for presenting a natural history of a disease, or one or more web services 414 for performing certain functions associated with presenting a natural history of a disease. The system may further comprise a user interface server 508 configured to host an application or web page configured to allow a user to interact with the web application 412 or web services 414 for presenting a natural history of disease. In such an embodiment, a service provider may provide hardware 102 and services 414 or applications 412 for use by a client without directly interacting with the client's customers.

Figure 6:
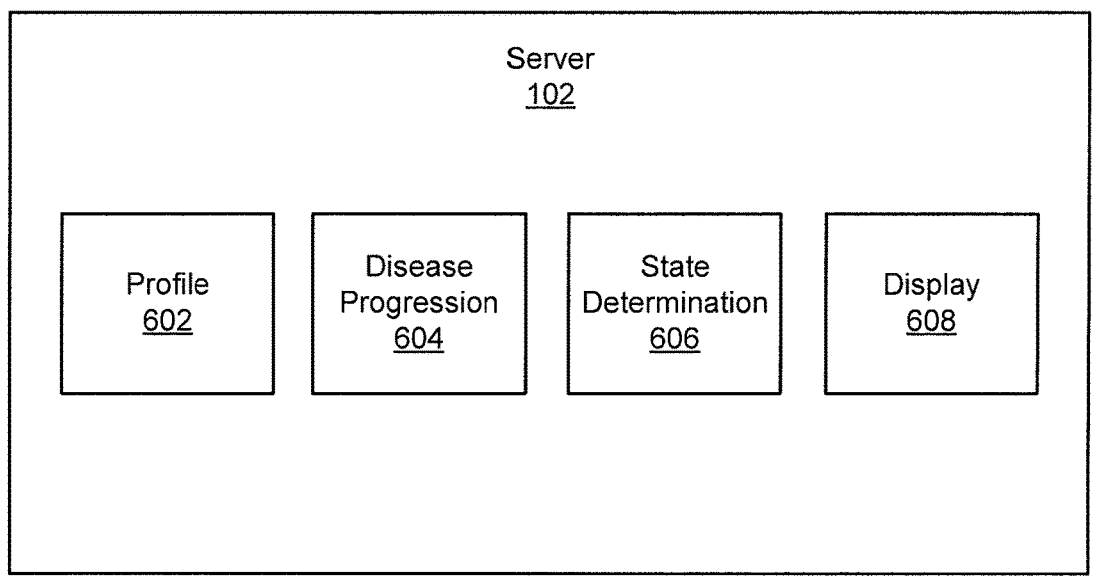
FIG. 6 is a schematic block diagram illustrating one embodiment of an apparatus for presenting a natural history and progression pathway of a disease.

FIG. 6 illustrates one embodiment of an apparatus 600 for presenting a natural history of a disease. In one embodiment, the apparatus 600 is a server 102 configured to load and operate software modules 602-608 configured for presenting a natural history of a disease. Alternatively, the apparatus 600 may include hardware modules 602-608 configured with analogue or digital logic, firmware executing FPGAs, or the like configured to generate a health profile for an individual, retrieve a disease progression map comprising one or more disease progression states from a data storage device, determine a disease progression state associated with the individual in response to the health profile, and display a graphical representation of the disease progression state with reference to the disease progression map. In such embodiments, the apparatus 600 may include a profile module 602, a disease progression module 604 a state determination module 606, and a display module 608.

In one embodiment, the profile module 602 is configured to generate a health profile for an individual. In a further embodiment, an input/output adapter 310 may receive information to generate a health profile for an individual. In a further embodiment, the input output adapter 310 may include a communications adapter 314 configured to receive input from a network 108. For example, the profile module 602 may generate the health profile based on insurance claims data, previously stored profile data, socioeconomic data, or the like. Alternatively, the profile module 602 may collect the health profile information from the user through an interactive display. The information used to generate the profile may include history of enrollment in a healthcare plan, demographic data, insurance claims data, lab data, pharmacy data including compliance level, race/ethnicity data, psychographic data, disability, absenteeism, workers compensation data, health risk assessment data, genetic tags, and the like. Further embodiments of the profile module 602 are described below with relation to FIG. 7.

In a certain embodiment, the server 102 may include a CPU 302 configured to retrieve a disease progression map comprising one or more disease progression states from a data storage device, and to determine a disease progression state associated with the individual in response to the health profile. In a particular embodiment, the CPU 302 may be configured to execute computer executable instructions configured in software modules. The software modules may be configured to cause the CPU 302 to retrieve a disease progression map comprising one or more disease progression states from a data storage device, and to determine a disease progression state associated with the individual in response to the health profile. For example, these software modules may include a disease progression module 604 and a state determination module 606.

In one embodiment, the disease progression module 604 is configured to retrieve a disease progression map comprising one or more disease progression states from a data storage device. For example, the user profile module 602 may receive some indication or identification of a disease with which the individual has been diagnosed. The disease progression module 604 may then retrieve disease progression data from a data storage device 104. In one embodiment, the disease progression data may include a disease progression map or graph. Alternatively, the disease progression module 604 may generate the disease progression map in response to the disease progression data retrieved from the data storage device 104. The disease progression data may include a chart, a table, a data listing, a database report, a graph, a timeline, or the like. In one particular embodiment, the disease progression map may include a decision or event tree style graph. The disease progression map is described in greater detail below with reference to FIG. 13.

In one embodiment, the state determination module 606 is configured to determine a disease progression state associated with the individual in response to the health profile. For example, as described in FIG. 13, a disease progression map may include one or more disease progression states. The state determination module 606 may then use the health profile information to determine a disease progression state within the disease progression map that most closely matches the individuals current health status. For example, the state determination module 606 may match certain diagnosis codes, medication prescriptions, symptoms, or the like to identify a predetermined disease progression state that is approximately a match for the individual's current state.

In one embodiment, the display module 608 is configured to display a graphical representation of the disease progression state with reference to the disease progression map. For example, the display module 608 may present a flag or indicator on the disease progression state that approximately matches the current status of the individual. In a particular embodiment, a display adapter 322 may be configured to receive information from the display module 608 and display a graphical representation of the disease progression state with reference to the disease progression map. In particular, the display adapter 322 may display the graphical representation on a computer monitor 324.

Figure 7:
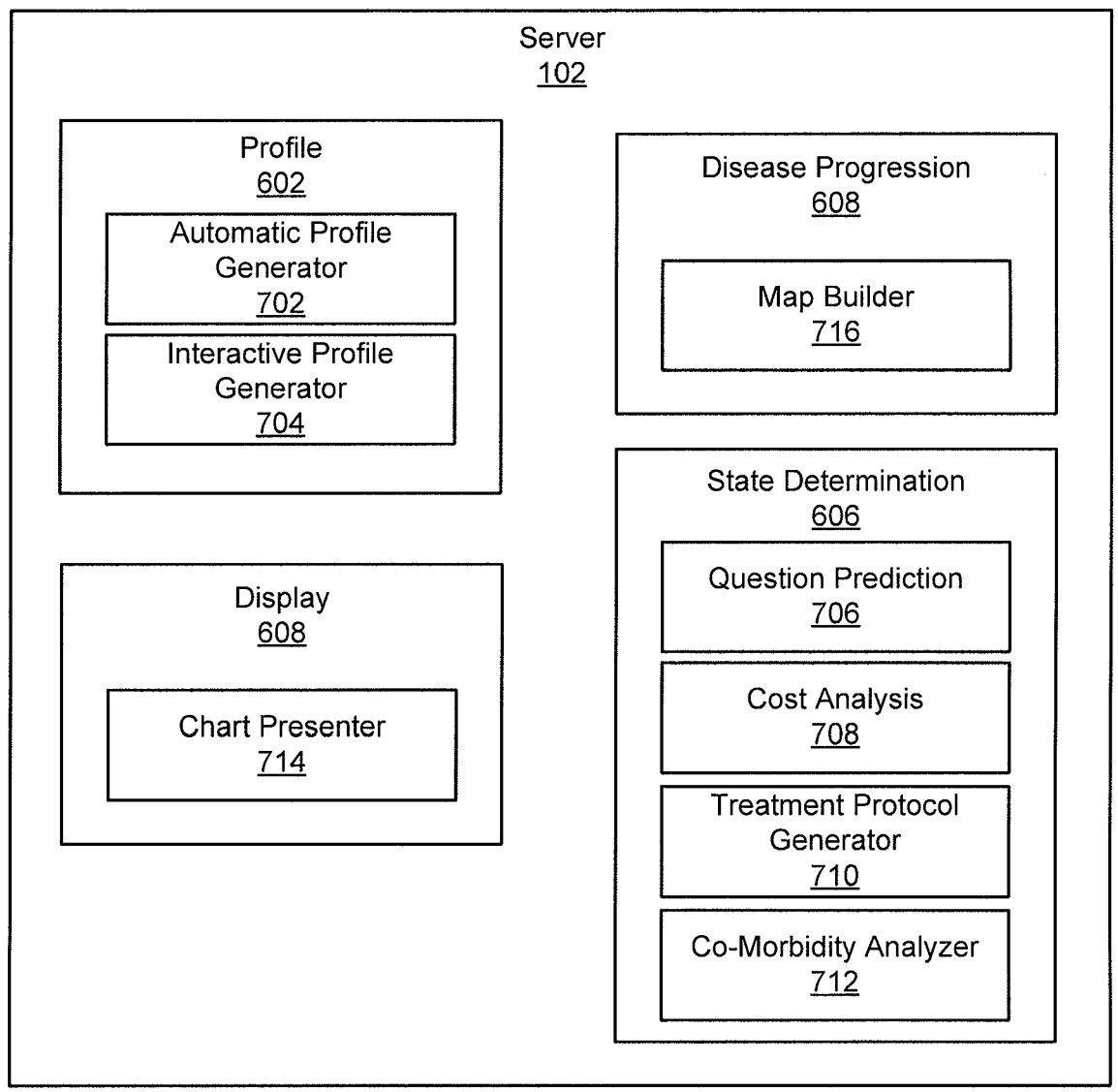
FIG. 7 is a schematic block diagram illustrating a further embodiment of an apparatus for presenting a natural history and progression pathway of a disease.

FIG. 7 illustrates a further embodiment of an apparatus 600 for presenting a natural history of a disease. The apparatus 600 may include a server 102 as described in FIG. 6.

In a further embodiment, the profile module 602 may include an automatic profile generator 702 and/or an interactive profile generator 704. In one embodiment, the profile module 602 may request a user identification credential, such as a login name and password. If the individual can be authenticated a secure connection may be established. The automatic profile generator 702 may then automatically generate the health profile for the individual from data previously stored in association with the individual. For example, the automatic profile generator 702 may query datasets 418-422 stored on various data storage devices 204-210 to collect user profile information including health insurance claims data, socio-economic data, gender/race data, health insurance plan enrollment histories, and the like.

Alternatively, if the user does not provide a valid credential, or there is no information stored in the data storage devices 204-210 that can be associated with the individual, then the interactive profile generator 704 may generate the health profile in response to data entered by a user regarding the individual through an interactive display. For example, the interactive profile generator 704 may generate a user-interactive web page, form, field, or set of questions used to elicit information required to build the health profile for the individual. For example, an interactive form may include questions regarding symptoms, diagnoses, medications, age, gender, race/ethnicity, and the like.

In a further embodiment, the disease progression module 604 may include a disease progression map builder 716. The disease progression map builder 716 may be configured to generate the predetermined disease progression maps. In one embodiment, the disease progression data and/or disease progression map may be generated through a data-mining process. For example, a database comprising insurance claim information history of enrollment in a healthcare plan, demographic data, insurance claims data, lab data, pharmacy data, race/ethnicity data, psychographic data, disability, absenteeism, workers compensation data, and the like may be stored for a large number of customers of a health insurance company or the like. In a particular embodiment, such a database may include historical data spanning ten or more years for several million customers. In such an embodiment, the breadth and depth of the database may provide detailed information regarding a large number of diseases and their associated stages, treatments, and outcomes.

For example, a disease progression map may be generated for adult-onset, type II diabetes. In such an embodiment, disease progression map builder 716 or a separate device or process may query one or more datasets 418-422 containing insurance claims data, lab data, pharmacy data, and other data associated with up to several million individuals. The query may include terms for identifying individuals who have a health administration code (e.g., an ICD9™ code) associated with a diagnosis for diabetes. The disease progression map builder 716 may then search for information in the other data sets 418-422 to identify additional information for the individuals who have been diagnosed with diabetes.

In such an embodiment, the disease progression map builder 716 establishes a scaling parameter for the disease progression map. For example, the scaling parameter may be time increments, disease progression stages, disease progression states, or the like. In this example, the scaling parameter may be time. In such an embodiment, the disease progression map builder 716 may then align the disease progression information according to a date of diagnosis, and normalizing the data so that the various disease progression states may be aligned or analyzed in according to a normalized time frame.

For example, a first individual may have been diagnosed with diabetes in February, 2005 and a second individual may have been diagnosed with diabetes in November, 2005. In such an embodiment, the date of diagnosis for both the first individual and the second individual may be aligned and normalized (e.g., to 2005) so that the dates of various subsequent codes or disease progression states match, or are aligned to a normalized time frame. In such an embodiment, the various decisions, lab tests, treatments, procedures, prescriptions, and the like may be positioned on a single map to show the various states and resulting The disease progression map builder 716 may then determine an association of the various disease progression states, and the resulting bifurcations and end results of various decisions made at the various disease progression states may then be determined. This information may be compiled and aggregated for the identified individuals, and a consolidated disease progression map or presentation of the natural history of the disease may be established from or before the time of diagnosis up through various times of cures or death. In a further embodiment, pre-disease information may be analyzed to determine certain precursors or events that may have lead to the disease. Such an embodiment, may allow a health care professional to determine how he/she may have intervened to prevent the disease. A further embodiment of a disease progression map is described below with reference to FIG. 13.

Disease progression data and/or disease progression maps may be stored in the data storage device 104. This same process may be iteratively performed for a set of diagnosis codes to generate a set of predetermined diseases progression maps. In an alternative embodiment, these various steps, or a subset of these steps, may be performed on demand, although this process may be more time consuming to an end user than generating and storing the disease progression maps in advance.

In a further embodiment, the state determination module 606 may include a question prediction module 406 configured to predict one or more questions that the individual may have regarding their health state in response to the determination of the disease progression state associated with the individual. For example, the question prediction module 706 may use information associated with the individual's disease progression state, including the various paths that may result from that disease progression state to determine likely issues, symptoms, decisions, or the like that the individual may be facing. For example, a person who has just been diagnosed with diabetes may be wondering how to find a specialist in diabetes, a person with advanced diabetes may be wondering what his/or her life expectancy may be, or the like. The question prediction module 706 may be able to artificially identify common questions based on the individual's disease progression state, and then present helpful information that may resolve such questions.

In one embodiment, the state determination module 606 may also include a cost analysis module 708 configured to analyze costs associated with one or more disease progression scenarios based on the disease progression state associated with the individual. For example, the cost analysis module 708 may determine one or more disease progression paths that may result from the disease progression state at which the individual is positioned. The cost analysis module 708 may then retrieve cost information from historical insurance claim data, price lists, or other sources to determine the cost associated with each of the disease progression paths. In one embodiment, the cost analysis module 708 may compare costs of two separate disease progression paths, or two options at a disease progression state.

In one embodiment, the state determination module 606 may also include a treatment protocol generator 710 configured to determine an optimized treatment protocol for the individual in response to the disease progression state associated with the individual. For example, the treatment protocol generator 710 may compare one or more actions or treatment decisions and move through several possible disease progression paths to determine which path or decision yields an optimum result. In this example, the treatment protocol generator may move through the disease progression states as though the disease progression map were a decision tree optimization graph. The treatment protocol generator 710 may evaluate each path to an end result at each disease progression state until the optimum result is obtained. In such an example, the optimum result may include a total cure of the disease. Alternatively, the optimum result may include a most cost efficient management of a disease, or the like.

In one embodiment, the state determination module 606 may also include a co-morbidity analyzer 712 configured to identify a potential co-morbidity with an increased probability of presentation as a result of the disease progression state associated with the individual. For example, the co-morbidity analyzer 712 may identify a cause of death from insurance claim data, government records, or the like associated with the individuals identified in the disease progression data. Alternatively, the co-morbid conditions may be identified in advance and stored with the disease progression data. In such an embodiment, the co-morbidity analyzer 712 may generate a list of co-morbid conditions that one suffering from a specified disease may encounter. For example, the co-morbidity analyzer 712 may determine that individuals suffering from diabetes may also have an increased likelihood of suffering from kidney failure.

In a further embodiment, the display module 608 may include a chart presenter 714 configured to display one or more graphical charts representing information generated by the state determination module. For example, the chart presenter may retrieve disease progression data from the data storage device 104 including life expectancy data, cost data, or the like and generate graphs for displaying the disease progression data to a user. Alternatively, the chart generator 714 may receive data from the question prediction module 706, the cost analysis module 708, the treatment protocol generator 710, or the co-morbidity analyzer 712 and generate the graphs based on that data. The graphs may be generated according to one or more predetermined graph templates or formats.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 8:
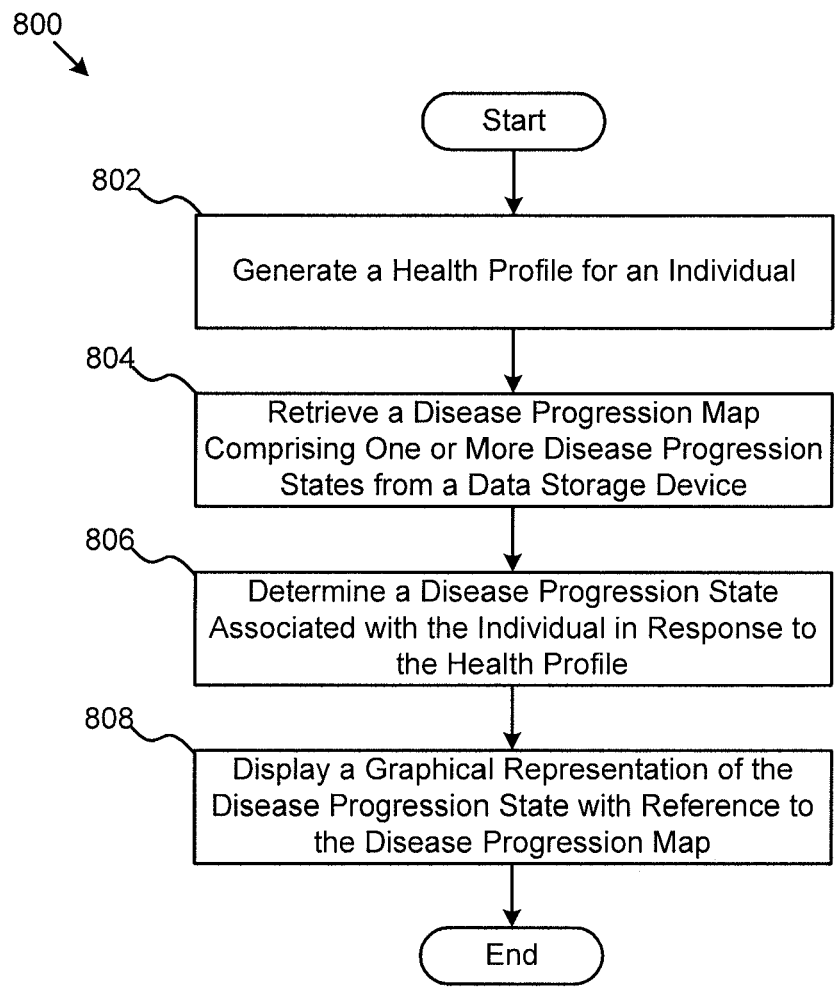
FIG. 8 is a schematic flow chart diagram illustrating one embodiment of a method for presenting a natural history and progression pathway of a disease in accordance with the present invention.

FIG. 8 illustrates one embodiment of a method 800 for presenting a natural history of a disease. In one embodiment, the method 800 starts when the profile module 602 generates 802 a health profile for an individual. The disease progression module 604 may then retrieve 804 a disease progression map comprising one or more disease progression states from a data storage device 104. In a further embodiment, the state determination module 606 may determine 806 a disease progression state associated with the individual in response to the health profile generated 802 by the profile module 602. The method 800 may end when the display module 608 displays 808 a graphical representation of the disease progression state with reference to the disease progression map.

Figure 9:
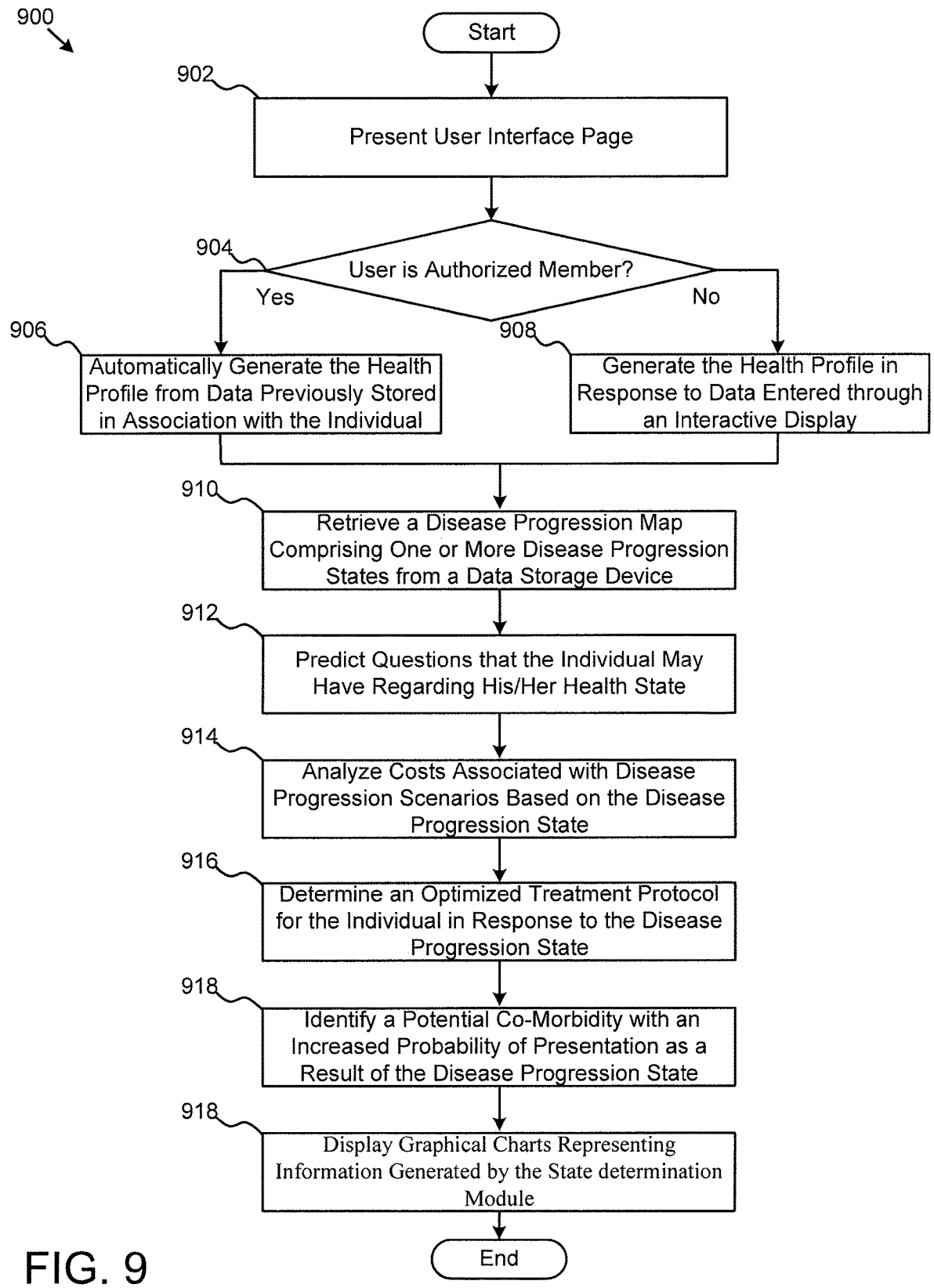
FIG. 9 is a schematic flow chart diagram illustrating a further embodiment of a method for presenting a natural history and progression pathway of a disease in accordance with the present invention.

FIG. 9 illustrates a further embodiment of a method 900 for presenting a natural history of a disease. In one embodiment, the method 900 starts when the profile module 602 presents 902 a user interface page. The profile module 602 may then determine 904 whether the individual is an authorized member of the service or of a health care plan. If the user is an authorized member, then the automatic profile generator 702 may automatically generate 906 a health profile from data previously stored in association with the individual (e.g., claims data, gender, age, etc.). If the user is not an authorized member, the interactive profile generator 704 may generate 908 the health profile in response to data entered by the user through an interactive display.

In a further embodiment, the disease progression module 910 may then retrieve 910 a disease progression map comprising one or more disease progression states from a data storage device 104. The question prediction module 706 may then predict 912 one or more questions that the individual may have regarding his/her health state. In a further embodiment, the cost analysis module 708 may analyze 914 costs associated with one or more disease progression scenarios based on the disease progression state at which the individual is located. In still a further embodiment, the treatment protocol generator 710 may determine 916 an optimized treatment protocol for the individual in response to the disease progression state at which the individual is located. Finally, the co-morbidity module 712 may identify 918 a potential co-morbidity condition that has an increased probability of presentation as a result of the disease progression state.

In one embodiment, the method 900 may end when the chart presenter 714 displays 918 a graphical chart representing information generated by the various modules 706-712 of the state determination module 606.

Figure 10:
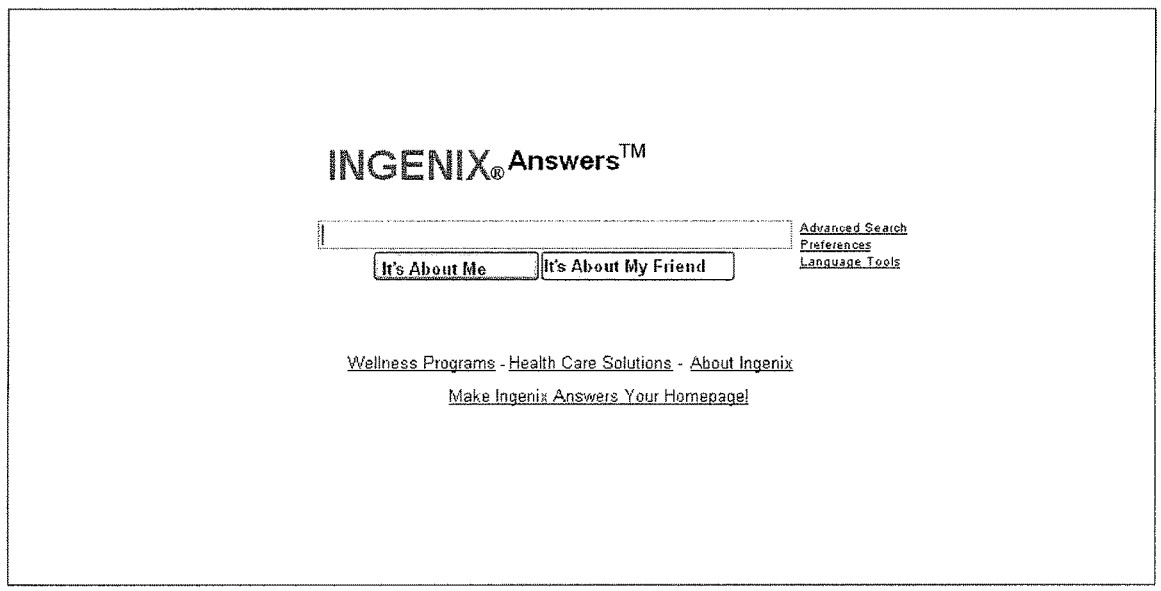
FIG. 10 is a screen-shot diagram illustrating one embodiment of a user interface display.

FIGS. 10 and 11 illustrate embodiments of user interactive web pages or forms that may be generated by the profile module 602 for interacting with a user. For example, FIG. 10 illustrates one embodiment of an interactive profile collection form 1000 that may receive health profile information related to an individual. For example, the user may enter a disease, a diagnosis code, a symptom, or the like. The user may then click "it's about me" or "it's about a friend." If the user enters "it's about me" the user may be prompted for authentication information such as a login name and password. If the user clicks "it's about a friend" or "I'm not a member" the interactive profile generator 704 may present one or more interactive forms or web pages for collecting health profile information.

FIG. 11 illustrates a display results page 1100 that may be generated by the display module 608. In the depicted example, the results page may include a section that prompts for information or displays answers regarding questions that have been predicted by the question prediction module 706. Additionally, the results pate 1100 may include links to graphs, links to the disease progression map, links to cost information and cost estimation tools, and physician information related to physicians that specialized in the identified disease.

Figure 12:
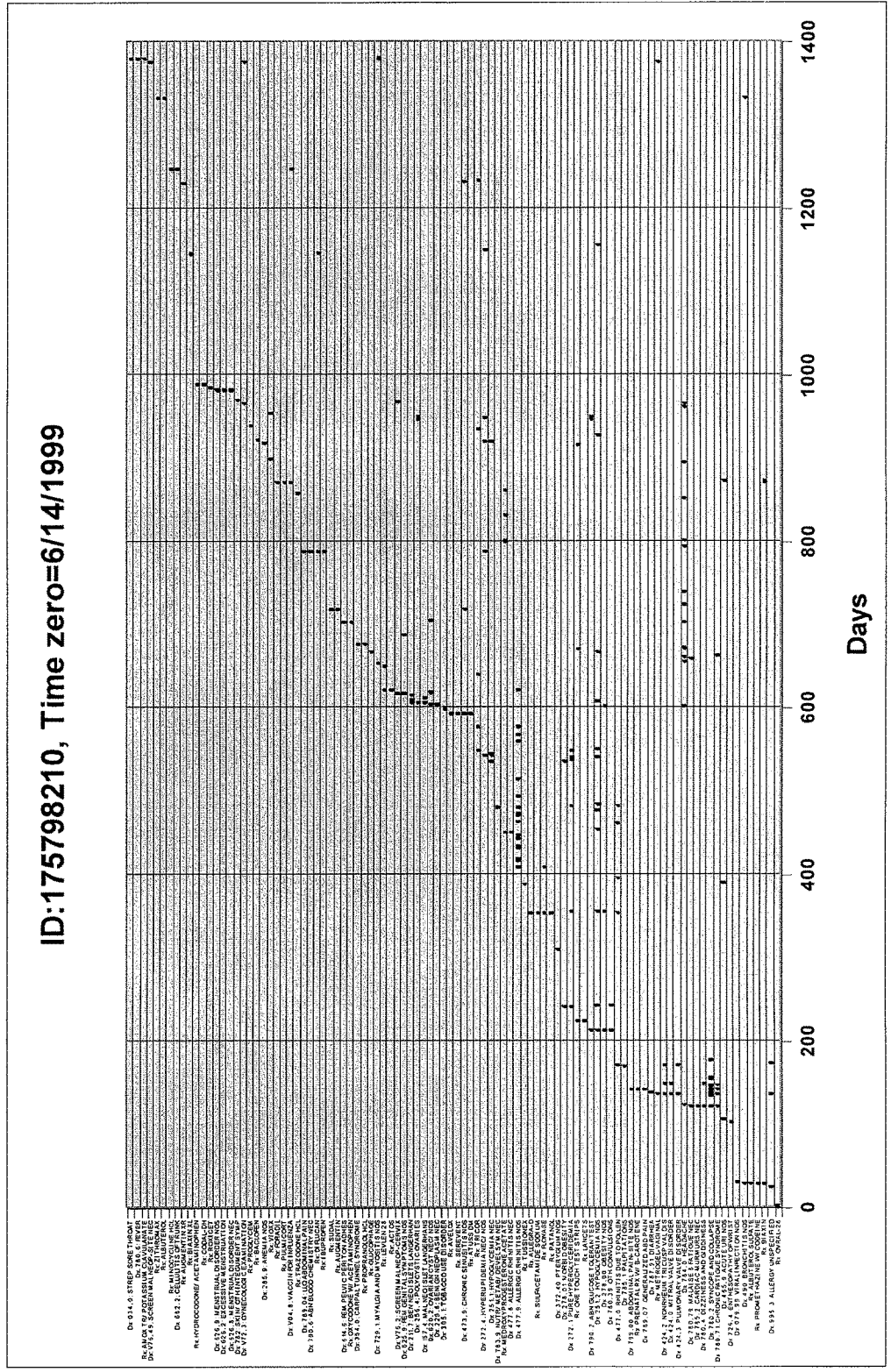
FIG. 12 is a graphical representation of a health profile associated with an individual.

FIG. 12 illustrates one embodiment of a health profile 1200 associated with an individual. The health profile 1200 may include a listing of various insurance codes and other information that is arranged in graphical or tabular format according to a time from diagnosis. Alternative scaling may be employed, and one of ordinary skill in the art will recognize alternative profile organization schemes.

Figure 13:
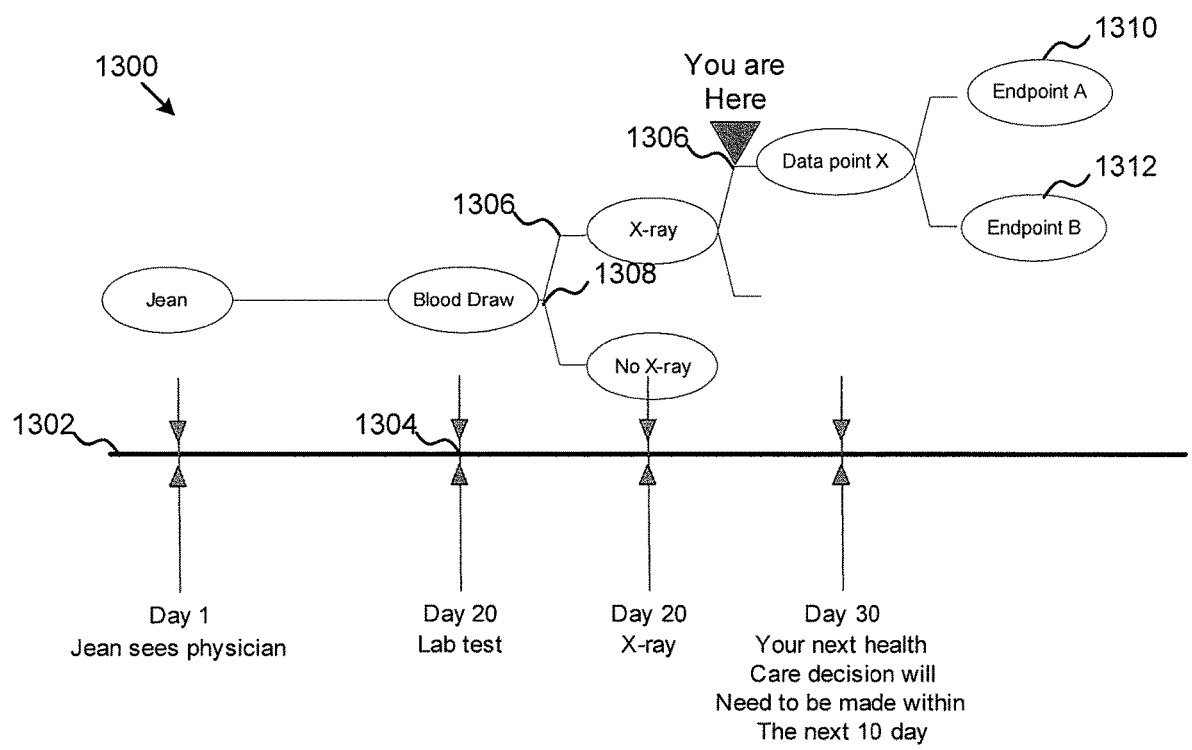
FIG. 13 is a graphical representation of one embodiment of a disease progression map for presenting a natural history and progression pathway of a disease.

FIG. 13 illustrates one embodiment of a presentation 1300 of a natural history of disease. In one embodiment, the presentation 1300 may include a disease progression map 1302 divided into a plurality of segments 1304. The presentation 1300 disease progression map 1302 may include a graphical representation of the disease progression that may include one or more bifurcated decision points or events 1308 and one or more disease progression states 1306. In a specific embodiment, the state determination module 606 may use the health profile information 1200 to determine which disease progression state 1306 the individual has reached and present a flag or indicator at that disease progression state 1306. For example, the flag or indicator in the depicted embodiment is an arrow and text that states "you are here."

Figure 14:
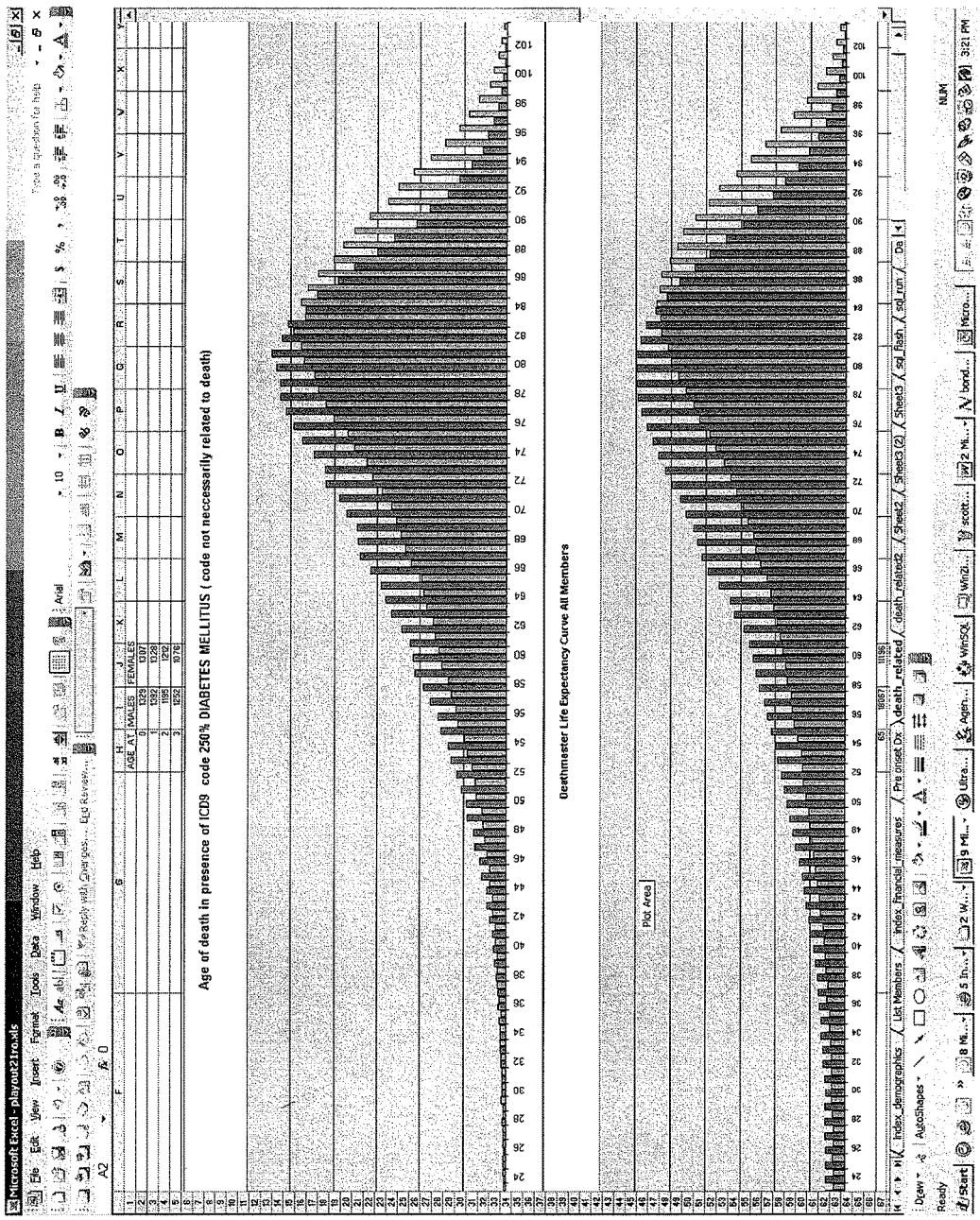
FIG. 14 is a screen-shot diagram illustrating one embodiment of a graphical chart for presenting information associated with the natural history and progression pathway of a disease.
Figure 15:
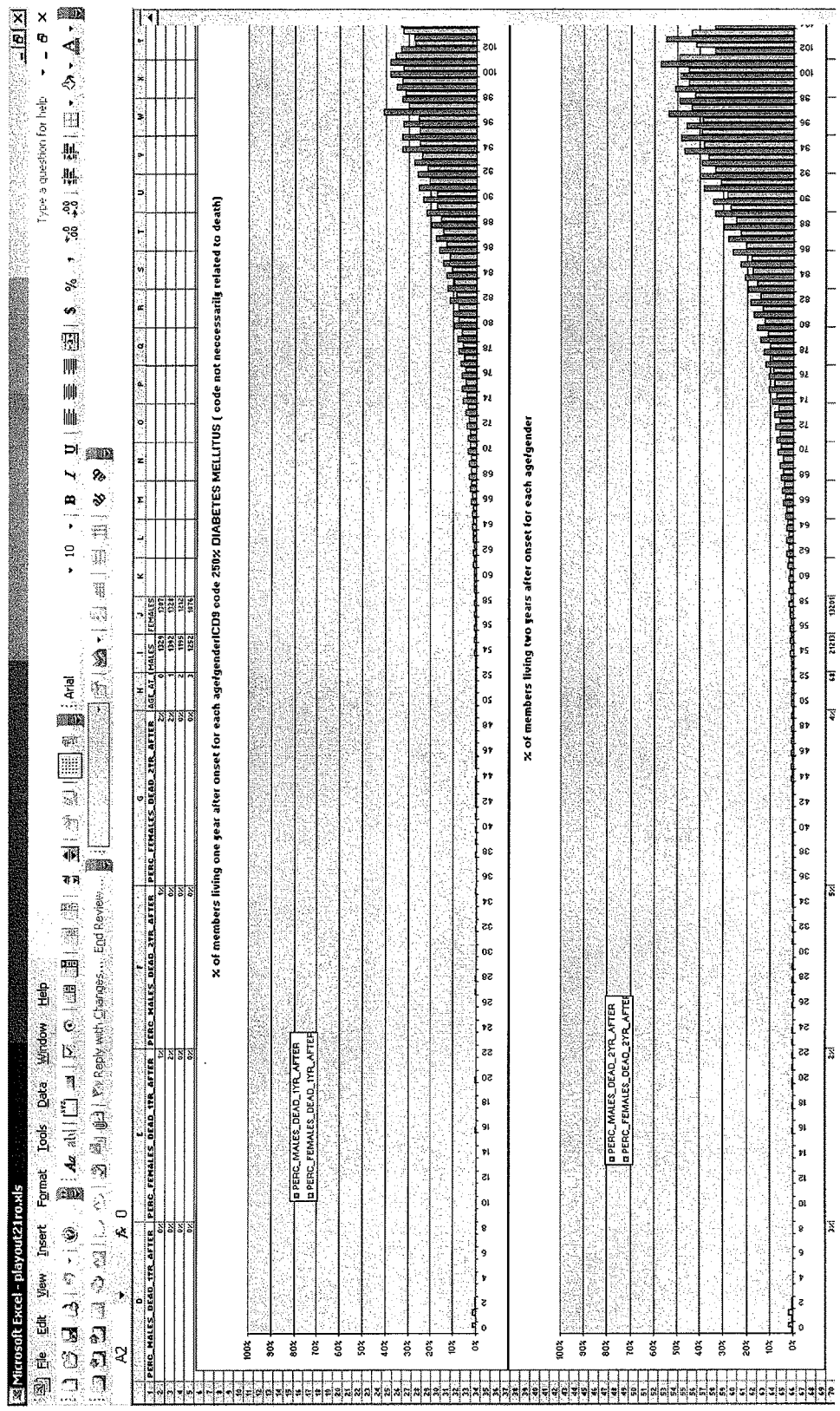
FIG. 15 is a screen-shot diagram illustrating another embodiment of a graphical chart for presenting information associated with the natural history and progression pathway of a disease.
Figure 16:
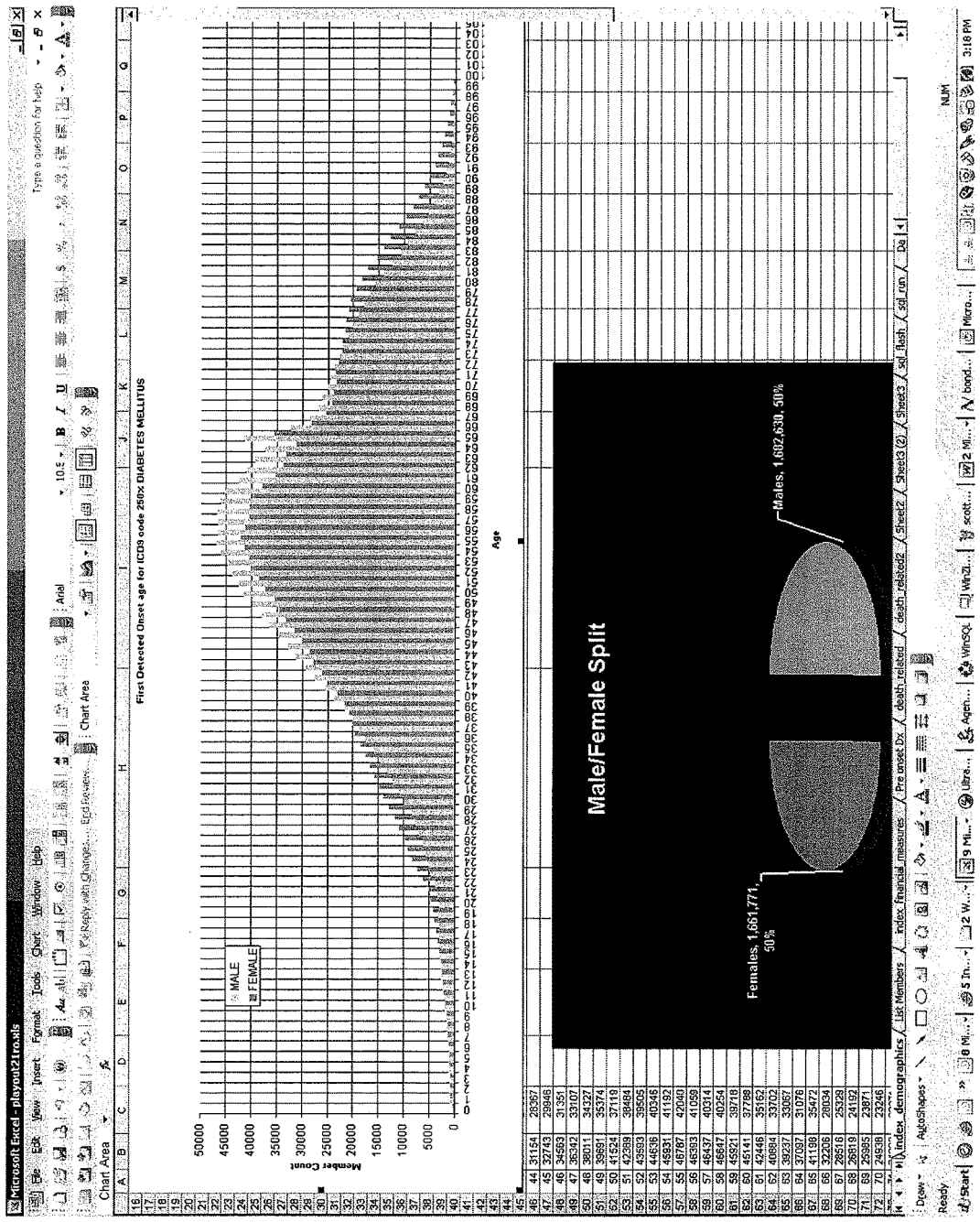
FIG. 16 is a screen-shot diagram illustrating another embodiment of a graphical chart for presenting information associated with the natural history and progression pathway of a disease.

FIGS. 14-16 illustrate various embodiments of graphs or charts that may be generated and displayed by the chart presenter 714. For example, the chart presenter 714 may present an age of death comparison chart 1400 that illustrates the average age of date in the presence of the diagnosis and a comparison chart that illustrates an average age of death for the general population. FIG. 15 illustrates a survivability graph 1500 that illustrates a number of individuals that survive one year or two years from the date of diagnosis. FIG. 16 illustrates a demographic chart configured to illustrate demographics related to the onset of the disease, including average age of onset and percent of male/female onset.

Figure 17:
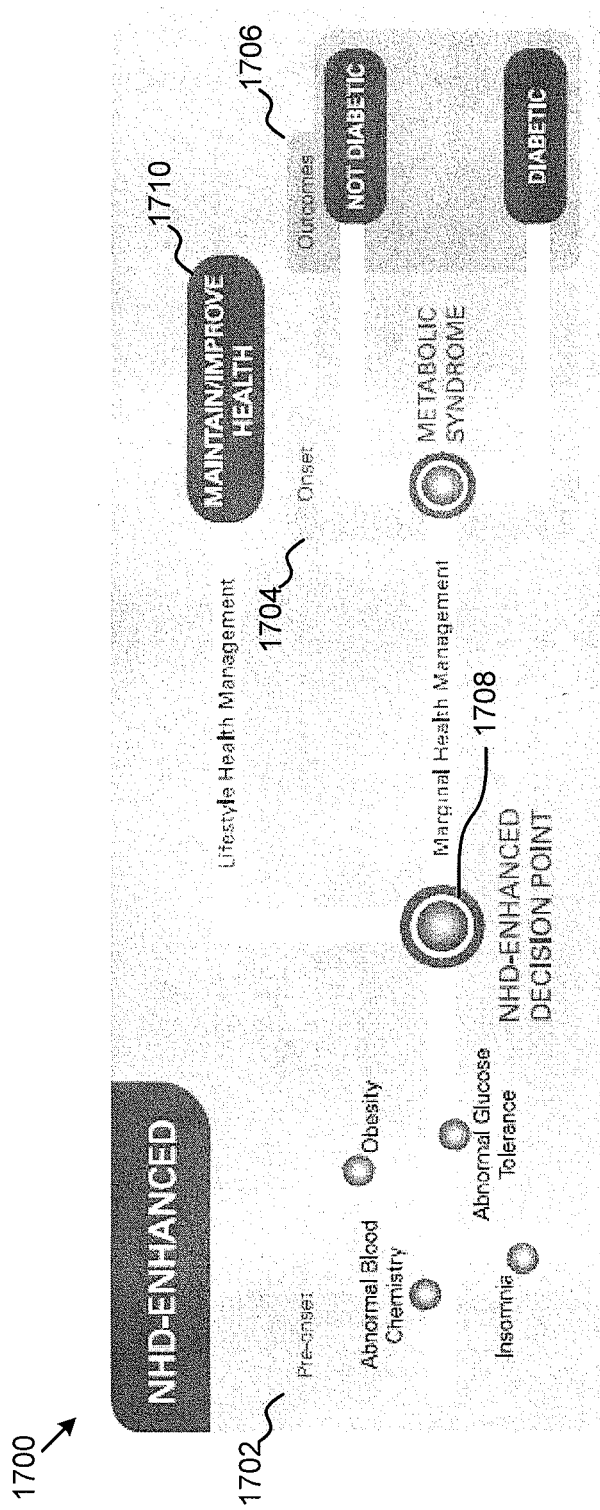
FIG. 17 is a graphical representation of a natural history of disease enhanced progression pathway of a disease.

FIG. 17 is a graphical representation of a natural history of disease enhanced progression pathway 1700 of a disease. In one embodiment, a typical progression pathway of a disease includes certain pre-onset conditions 1702, onset 1704 of the disease, and one or more outcomes 1706. However, as described in FIG. 17, the typical progression pathway of a disease may be enhanced or modified in response to the natural history of disease system 100, apparatus 600, and methods 800, 900 of the present embodiments.

For example, the present embodiments may analyze the various pre-onset 1702 conditions, such as obesity, insomnia, abnormal glucose tolerance, and the like which make up the individuals health profile. The server 102 may then retrieve 804 a disease progression map comprising one or more disease progression states 1306 from a data storage device 104. The server 102 may then determine a disease progression state 1306 associated with the individual. Then, the server 102 may generate a lifestyle health management plan and present options for avoiding onset 1704 of the disease at the NHD-enhanced decision point 1708. If, at the NHD-enhanced decision point 1708, the individual chooses to implement the suggested lifestyle health management plan, an alternative outcome 1710 may result.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

What is claimed is:

1. A relationship management device including a user interface providing a treatment protocol for an individual comprising:
   a user interface electrically connected with a data storage device configured to store one or more data sets comprising histories of a plurality of individuals;
   a server electrically connected with the user interface and the data storage device, wherein the server is configured to:
      generate a profile for an individual from relevant data previously stored in the data storage device in association with the individual, or generate a profile for an individual having no data stored in the data storage device from relevant data entered through the user interface;
      determine using at least one dataset to determine a plurality of historical twins for the individual, the historical twins having similar histories as the individual;
      generate a progression map based on histories of the plurality of historical twins, the progression map comprising one or more progression states; and
      determine a progression state associated with the individual in response to the profile with reference to the progression map; and
   a treatment processor electrically connected with the server, wherein the treatment processor is configured to generate a treatment protocol for the individual based on the progression state.

2. The relationship management device of claim 1, further configured to automatically generate the profile for the individual from relevant data previously stored in association with the individual.

3. The relationship management device of claim 1, further configured to generate the profile in response to relevant data entered by a user regarding the individual through an interactive display.

4. The relationship management device of claim 1, further comprising a question predictor module configured to predict one or more questions that the individual may have regarding their state in response to the determination of the progression state associated with the individual.

5. The relationship management device of claim 1, further comprising a display module configured to graphically display the progression state associated with the individual with reference to the progression map.

6. The relationship management device of claim 1, further configured to communicate the treatment protocol to a physician for the individual.

7. The relationship management device of claim 1, further configured to identify a potential co-morbidity with an increased probability of presentation as a result of the progression state associated with the individual.

8. The relationship management device of claim 1, further configured to display one or more graphical charts representing information generated by a state determination module.

9. The relationship management device of claim 8, wherein the information generated by the state determination module is a progression state associated with the individual.

* * * * *